US 12,287,764 B2

(12) United States Patent
Nazari et al.

(10) Patent No.: US 12,287,764 B2
(45) Date of Patent: Apr. 29, 2025

(54) FASTQ/FASTA COMPRESSION SYSTEMS AND METHODS

(71) Applicant: Rajant Health Incorporated, Malvern, PA (US)

(72) Inventors: Foad Nazari, Malvern, PA (US); Sneh Patel, Malvern, PA (US); Emma K. Murray, Malvern, PA (US); Giana J. Schena, Malvern, PA (US)

(73) Assignee: Rajant Health Incorporated, Malvern, PA (US)

( * ) Notice: Subject to any disclaimer, the term of this patent is extended or adjusted under 35 U.S.C. 154(b) by 0 days.

(21) Appl. No.: 17/990,361

(22) Filed: Nov. 18, 2022

(65) Prior Publication Data

US 2024/0134825 A1     Apr. 25, 2024

Related U.S. Application Data

(60) Provisional application No. 63/409,993, filed on Sep. 26, 2022, provisional application No. 63/280,721, filed on Nov. 18, 2021.

(51) Int. Cl.
  *G06F 16/00*    (2019.01)
  *G06F 16/16*    (2019.01)
  *G06F 16/174*   (2019.01)

(52) U.S. Cl.
  CPC ........ *G06F 16/1744* (2019.01); *G06F 16/162* (2019.01)

(58) Field of Classification Search
  None
  See application file for complete search history.

(56) References Cited

U.S. PATENT DOCUMENTS

| | | | | |
|---|---|---|---|---|
| 8,856,089 | B1* | 10/2014 | Briggs | G06F 16/2315 |
| | | | | 707/705 |
| 9,292,327 | B1* | 3/2016 | von Thenen | G06F 11/1484 |
| 9,424,185 | B1* | 8/2016 | Botelho | G06F 12/0253 |
| 10,554,220 | B1* | 2/2020 | Constantinescu | H03M 7/607 |
| 10,972,742 | B2* | 4/2021 | Gisquet | H04N 19/124 |
| 11,068,444 | B2* | 7/2021 | Sharangpani | G06F 16/24573 |
| 11,081,208 | B2* | 8/2021 | Jaffe | G16B 30/00 |
| 2005/0025316 | A1* | 2/2005 | Pelly | H04L 9/0894 |
| 2005/0028192 | A1* | 2/2005 | Hooper | H04N 5/85 |
| | | | | 348/E7.055 |

(Continued)

OTHER PUBLICATIONS

Notification of Transmittal of The International Search Report and the Written Opinion of the International Searching Authority, or the Declaration, International Search Report, and Written Opinion of the International Searching Authority mailed May 9, 2024, in International Patent Application No. PCT/US2022/080163, 7 pages.

(Continued)

*Primary Examiner* — Hasanul Mobin
(74) *Attorney, Agent, or Firm* — BLANK ROME LLP (57) ABSTRACT

Systems and methods to analyze and significantly compress FastQ and/or FastA datasets are disclosed. The methodology includes algorithms to compress sequences, quality scores and identifiers of read files. The method relies on reducing the dimension and redundancy in genomic data in a unique and optimal way and in the binary format. The methodology also includes the decoding protocols to decompress the compressed data with zero loss.

20 Claims, 7 Drawing Sheets

(56) References Cited

U.S. PATENT DOCUMENTS

| | | | |
|---|---|---|---|
| 2008/0091698 A1* | 4/2008 | Cook | G06F 16/285 |
| 2010/0172543 A1* | 7/2010 | Winkler | G08G 1/017 |
| | | | 382/104 |
| 2012/0254333 A1* | 10/2012 | Chandramouli | G06F 40/10 |
| | | | 709/206 |
| 2013/0338934 A1* | 12/2013 | Asadi | G16B 30/00 |
| | | | 702/20 |
| 2017/0060896 A1* | 3/2017 | Ito | G06F 16/1744 |
| 2017/0237445 A1 | 8/2017 | Cox et al. | |
| 2018/0075262 A1* | 3/2018 | Auh | G06F 21/6227 |
| 2018/0152535 A1 | 5/2018 | Sade et al. | |
| 2018/0364949 A1* | 12/2018 | Aston | G06F 3/067 |
| 2019/0205542 A1* | 7/2019 | Kao | G06F 8/10 |
| 2019/0287655 A1* | 9/2019 | Wesselman | G16B 20/00 |
| 2021/0366576 A1* | 11/2021 | Bartov | G16B 40/20 |

OTHER PUBLICATIONS

Behjati et al., "What is next generation sequencing?" Arch Dis Child Educ Pract Ed 2013; 98:236-238.

* cited by examiner

Companion Selection:

| | | | left companion | | | | | | | | | right companion | | | |
|---|---|---|---|---|---|---|---|---|---|---|---|---|---|---|---|
| | A | C | G | T | A | C | G | T | A | C | G | T | A | C | G | T |
| | 25 | 20 | 30 | 60 | 60 | 60 | 60 | 70 | | | | | 70 | 60 | 35 | 50 |
| | 20 | 30 | 60 | 60 | 60 | 70 | 60 | | | | | | 60 | 35 | 50 | 25 |
| Dominant Frequency | 26 | 30 | 60 | 60 | 60 | 70 | 60 | 70 | | | | | 70 | 60 | 35 | 50 | 25 |
| Total Frequency | 61 | 69 | 85 | 90 | 102 | | | | | | | | 95 | 77 | 76 | 63 | 51 |
| kmer Frequency | | | | | 110 | | | | | | | | | | | |
| Existancy Ratio = Total Freq / kmer Freq | 0.55 | 0.63 | 0.77 | 0.82 | 0.93 | | | | | | | | 0.86 | 0.70 | 0.69 | 0.57 | 0.46 |
| Dominancy Ratio= Dominant Freq / Total Freq | 0.43 | 0.43 | 0.71 | 0.67 | 0.69 | | | | | | | | 0.74 | 0.78 | 0.46 | 0.79 | 0.49 |
| Final kmer & companions | | | G | | C | | | | A | C | G | T | G | | | |

Existency Threshold= 0.6
Dominancy Threshold= 0.5

FIG. 6

| # | kmer | l_comp | r_comp |
|---|---|---|---|
| 1 | GGTGTATGCA | CTACAGATGATAGGATGTTTCATGT | TCGGGGTAGTCCGAGT |
| 2 | ATTCCGATAGGC | CGGGGTAGTCCGAGTAACGTCGGGGC | CGAGAAGTGTGTGGGAACGAA |
| 3 | TAGATTACGCCGATG | GTGGGAAGAAGT | AATATGATAGTGAAATGGATTT |
| 4 | ACGATGTCTAGTG | GTGAGCTACAAGGTAGTAGTGTCGTGTAGT | ATGAGTT |
| 5 | GGGGTCTGCTCCT | | CCGGCGGGGTCGAAGAAGGTGGTGGTGTTGAAG |
| 6 | AAATGAGTGAGGC | TTTATAGATAGTTGGGTGGTTGGTGT | AGGAGTCCGAG |
| 7 | GCTTCCAATTAGG | GGTTGATATTGCTAGGGTGGC | TGCATGAGTAGGTGGC |
| 8 | GGCCTTGGTATGT | CGGAAGGCCTTTTGGACAGGTGGTGTGTGGT | GCTTCT |
| 9 | GAGAATAGGGAA | GTTTGGTCTAGGGTGTAGCCT | ATCAGTGAATGAAGCCT |
| 10 | CAGATAGTGAGGA | GAAATATTAGTGTGGGGGATGAAG | AAGTTGAGCCAATAA |
| 11 | ATTCGAAGCCTG | GGAGTAGTAAGTTACAATATGGGAGATT | GTAGGATAAG |
| 12 | GTCAGGCCACTA | GATGAGTTGCTAATACAATGCCA | CGGTGAAAAGAAAGATGAA |
| 13 | GAAATATGCTGT | GCGATGATTAGGTAGGGAAGT | GTGTCTAGTCTATT |
| 14 | GGAAACGCCATAT | GTCAGAAGCTTATGTTGTTTATGCGG | CGGGGGCACGA |
| 15 | CGATTCCTCCTTTT | CTTGGGGGT | |
| 16 | AGCAGATCATTTC | GGCTCAGAAGCACTGC | ATATGCTTCCGTGGAGTGTGGC |
| 17 | GTTTGGTATTGGG | GATCAGACGAAGAGGGGC | TTATGCAGGGGTTTTAT |
| 18 | CTTGGAGTTAGT | GTGAAACGGTAGG | GACAGGCGATTCTAGGATAGTCA |
| 19 | TTTGAGTTAGT | CTTTAGTGTGGTGTATGGTTATTATTG | TTGATTAGTC |
| 20 | GTTTGATAGTTCTGG | TCGAATGTGTGGTAGGGTGGGGG | GCAGTGAGCTAGTAGTAGAATGTTTA |
| 21 | CATCCATATAGTCACT | GGGGTAAGGCGAG | CCAGGTTATG |
| 22 | GTAGCGAAGGCTGCT | GTTGAGGTTGCGGGTCTGTTA | AGAAGTCATCAAAAGCTATTA |
| 23 | GTAGTAGTGATGCC | CTACGGAGGGCTCAGGGTGGG | AGCAGTAGGACTGG |
| 24 | AGTAGTCCCTGC | | TAAGGGAGGGTAGAGTG |
| 25 | GCTAAATACTTGAAGG | GGAGTGTGGGAGTCA | CGGGTGGGGATAGGATGA |

FIG. 7

FASTQ/FASTA COMPRESSION SYSTEMS AND METHODS

CROSS-REFERENCE TO RELATED APPLICATIONS

This application claims the benefit of U.S. Provisional App. No. 63/280,721, filed Nov. 18, 2021, and U.S. Provisional App. No. 63/409,993, filed Sep. 26, 2022, the entire contents of both of which are incorporated herein by reference.

BACKGROUND

With the recent advancement of Next Generation Sequencing (NGS) technologies, a significant amount of genomic data is being produced at a fast pace and low cost. It is estimated that 2-40 exabytes of data will be generated within the next decade. However, the storage technology is advancing at a much slower pace, causing technical and economic challenges for NGS data storage. Also, transmission of these gigantic datasets is very costly and timely which causes delay and limitation in employment of these datasets.

General-purpose compression methods (e.g., Gzip, Bzip2) perform poorly on genomic data compression. Meanwhile, each of the existing domain-specific compression methods (e.g., SPRING, LFastqC, DSRC2, LFQC, SeqSqueezel, Quip, FQZComp) has specific disadvantages, including low compression rate, computational inefficiency, lossy compression, quality score-base sequence encoding dependency, ignoring non-N irregular bases, rigid protocols, etc.

Therefore, because of the desire to store and transmit vast amounts of genomic data and the inadequacy of existing compression methods, there is a need for efficient, domain-specific methods for NGS data compression.

SUMMARY OF THE INVENTION

The disclosed embodiments provide a system for compressing genomic data in a more efficient and lossless manner. In certain embodiments, the system of the present invention will receive a data file comprised of sequence bases, quality scores, and identifiers and apply an optimization algorithm on the quality scores, sequence k-mers from the sequence bases, and the identifiers. The system will perform a dimensionality reduction on the sequence bases, mapping and ranking the quality scores, and storing a template of the identifier that is consistent across the data file. The system then encodes the optimized data of the file in binary and compresses in a lossless format.

In certain embodiments, the identifiers are comprised of sequencing run data and cluster data.

In other embodiments, the quality scores comprise the sequence of quality values for base sequences.

In yet other embodiments, the sequence bases are comprised of regular bases and irregular bases.

In other embodiments, the data file is a FastQ file or a FastA file.

In certain other embodiments, the optimization algorithm determines the optimal hyper-parameter values for each of the quality scores, the sequence k-mers from the bases, and the identifiers.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose. Several preferred embodiments of the invention are described for illustrative purposes, it being understood that the invention may be embodied in other forms not specifically shown in the drawings.

Next generation sequencing (NGS) analysis utilizes bioinformatics in order to convert signals from the machine to meaningful information that involve signal conversion to data, annotations or catalogued information, and actionable knowledge. The basic next-generation sequencing process involves fragmenting DNA/RNA into multiple pieces, adding adapters, sequencing the libraries, and reassembling them to form a genomic sequence. Millions or billions of DNA strands can be sequenced in parallel, yielding substantially more throughput and minimizing the need for the fragment-cloning methods. NGS can be used to expedite sequencing of an entire human genome in a short period of time. See Behjati S, Tarpey PS. What is next generation sequencing?. *Arch Dis Child Educ Pract Ed.* 2013; 98(6): 236-238. doi:10.1136/archdischild-2013-304340.

NGS results in the generation of a significant amount of genomic data. As such, the present technology is designed to compress sequences, quality scores, and identifiers of read files in a novel manner that allows for the more efficient storage of that data, while also providing decoding protocols to decompress the compressed data with substantially zero loss.

Figure 1:
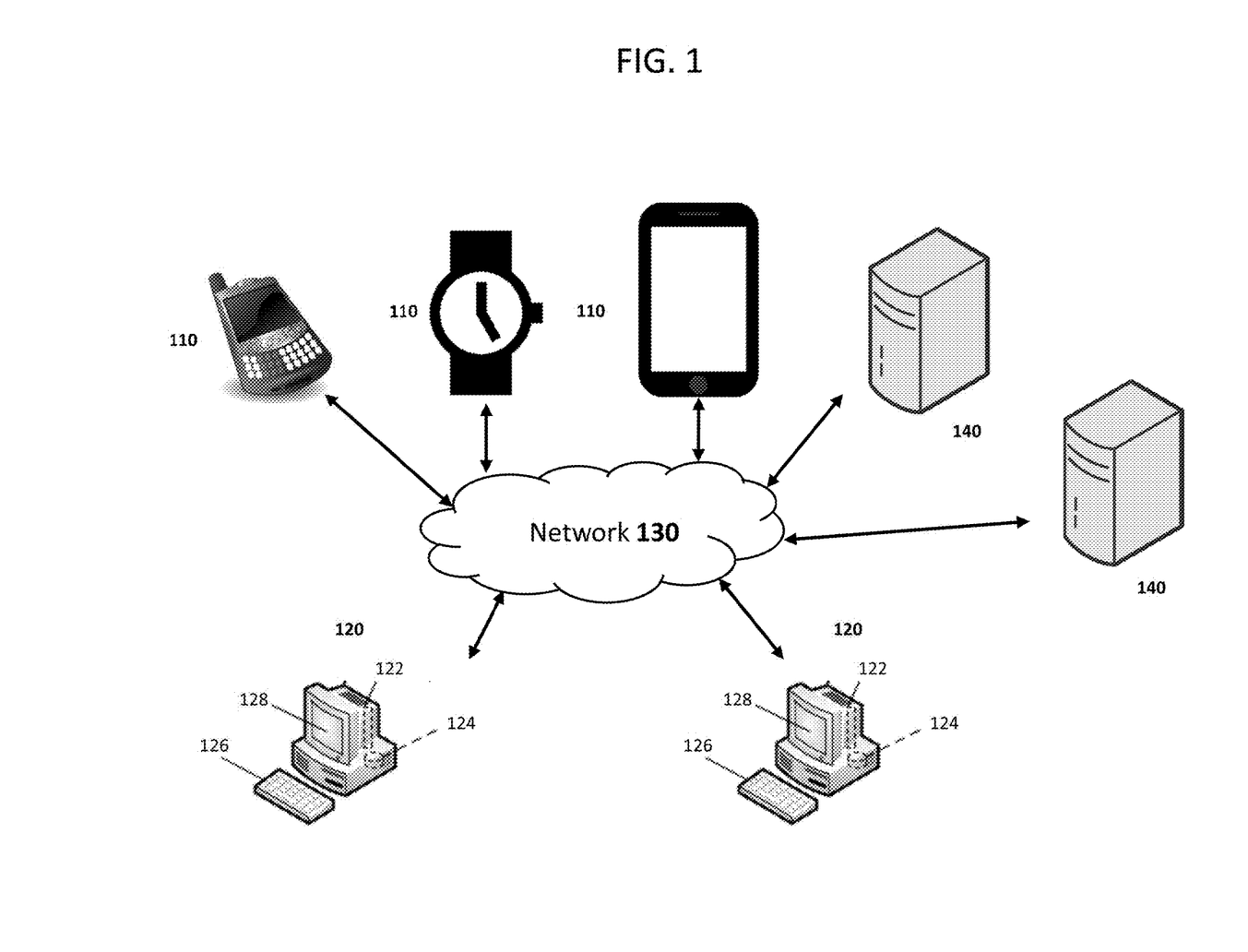
FIG. 1 is a diagram of an exemplary embodiment of the hardware of the system of the present invention.

FIG. 1 is an exemplary embodiment of the system of the present invention. In the exemplary system 100, one or more peripheral devices 110 are connected to one or more computers 120 through a network 130. Examples of peripheral devices/locations 110 include smartphones, tablets, wearables devices, and any other electronic devices that collect and transmit data over a network that are known in the art. The network 130 may be a wide-area network, like the Internet, or a local area network, like an intranet. Because of the network 130, the physical location of the peripheral devices 110 and the computers 120 has no effect on the functionality of the hardware and software of the invention. Both implementations are described herein, and unless specified, it is contemplated that the peripheral devices 110 and the computers 120 may be in the same or in different physical locations. Communication between the hardware of the system may be accomplished in numerous known ways, for example using network connectivity components such as a modem or Ethernet adapter. The peripheral devices/locations 110 and the computers 120 will both include or be attached to communication equipment. Communications are contemplated as occurring through industry-standard protocols such as HTTP or HTTPS.

Each computer 120 is comprised of a central processing unit 122, a storage medium 124, a user-input device 126, and a display 128. Examples of computers that may be used are: commercially available personal computers, open source computing devices (e.g. Raspberry Pi), commercially available servers, and commercially available portable devices (e.g. smartphones, smartwatches, tablets). In one embodiment, each of the peripheral devices 110 and each of the computers 120 of the system may have software related to the system installed on it. In such an embodiment, system data may be stored locally on the networked computers 120 or alternately, on one or more remote servers 140 that are accessible to any of the peripheral devices 110 or the networked computers 120 through a network 130. In alternate embodiments, the software runs as an application on the peripheral devices 110, and includes web-based software and iOS-based and Android-based mobile applications.

Figure 2:
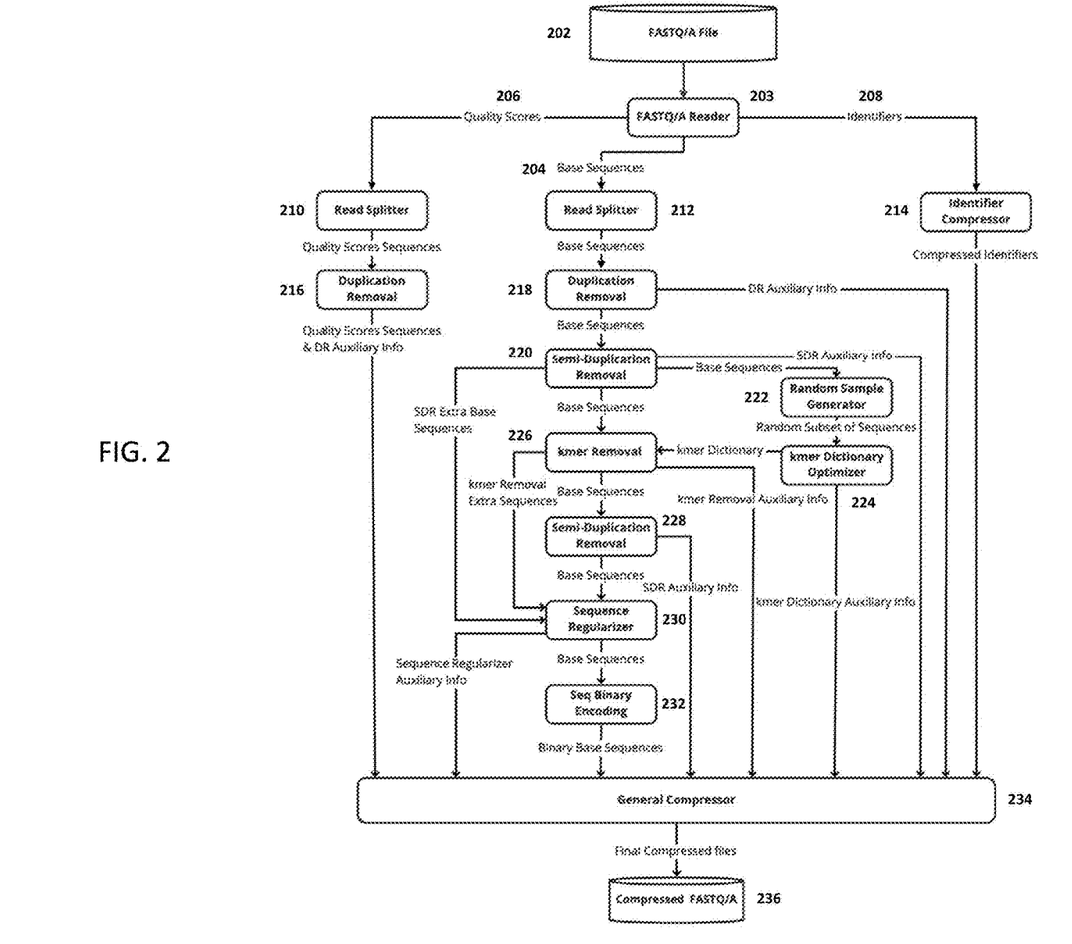
FIG. 2 is a flowchart of a process used to compress genomic data in accordance with an exemplary embodiment of the present invention.

FIG. 2 is a flow diagram illustrating a process for compressing a raw FastQ/A file 202 to generate a compressed FastQ/A file 236. FastA refers to a text-based format for representing either nucleotide sequences or amino acid (protein) sequences, in which nucleotides or amino acids are represented using single-letter codes. FastQ refers to a file format that stores the nucleotide base sequences, the calculated confidence for each base in a sequence, and information describing the origin of the read down to its position on the sequencing platform flow-cell. FastA files may be compressed instead of or in addition to raw FastQ/A files 202. FastA files include only the identifier and sequence bases. The process is comprised of two main stages: domain specific compression and general compression. The compressor aims to recognize the redundant and similar patterns in FastQ/A data and use them for lossless compression of datasets in binary. The process commences at the FastQ file 202, which is transmitted to the FastQ/A Reader 203 where the reader loads and reads the file 202. The FastQ/A file is comprised of sequence bases 204, quality scores 206, and identifiers 208. The identifiers 208 include information about the sequencing run and the cluster. The bases 204 comprise the sequence of base calls. The quality scores 206 comprise the sequence of quality values for base sequences, typically with one quality value for each base 204. The FastQ/A Reader 203 loads and reads the base sequences 204, quality score sequences 206, and the identifiers 208 in FastQ/A file 202 to memory and creates the base sequences, quality score sequences, and identifier reads.

In DNA/RNAs, there are nucleotides other than A, C, G, T and U, such as N, R, W, as shown in Table 1. Those bases are known as irregular bases. In this method, all irregular bases associated with the bases 204 are stored temporarily as "A" in the Regular Bases. The system detects and stores the type and location of each irregular base 216 in the FastQ/A dataset. When there are no irregular bases in the FastQ dataset, that file may be excluded. When one-to-one or many-to-one mapping from the quality scores 206 to the irregular bases is possible in the dataset, that quality score 206 can be employed for localizing the irregular bases. If not, then that file is created. Another scenario that would result in the creation of that file is when a FastA file is being compressed.

TABLE 1

IUPAC (International Union of Pure and Applied Chemistry) single letter codes

| DNA/RNA Symbol | Name | Remarks |
| --- | --- | --- |
| A | Adenine | Purine |
| G | Guanine | Purine |
| C | Cytosine | Pyrimidine |
| T | Thymine | Pyrimidine |
| U | Uracil | Pyrimidine |
| R | Purine | A or G |
| Y | Pyrimidine | C or T/U |
| M |  | A or C |
| K |  | G or T |
| S | Strong | C or G |
| W | Weak | A or T |
| H | Not G | A or C or T |
| B | Not A | C or G or T |
| V | Not U/T | A or C or G |
| D | Not C | A or G or T |
| N | Ambiguous | A or C or G or T |

The system performs a template comparison, which comprises storing the template of the identifier 208, which is consistent over the sample/dataset. Then, the variables are encoded. Since not all variables change from read to read, the template comparison first checks to determine if the variable has changed, and, if so, stores the differences in variables from the previous read.

The optimizer 210 conducts a statistical analysis on the distribution of each of the quality scores 206, the sequence k-mers from the bases 204, and the identifier variables 208. k-mers are substrings of length k contained with a base sequence. In certain embodiments, an optimization algorithm is separately applied for each of the quality scores 206, the sequence k-mers from the bases 204, and the identifier variables 208. The optimization variables are hyperparameters of the blocks downstream. The system employs a mathematical formulation, based on the encoding protocol for the optimizer's 210 objective function, which is a function of protocol hyperparameters and dataset distribution indices. That objective function has a direct relation to the compression rate and is minimized by the optimizer 210. The result of that optimization process shapes the protocol for each dataset, adaptively and optimally.

Statistical characteristics of components of quality scores, sequences and identifier variables vary from one dataset to another. The performance of redundancy-based compressors depends on the frequency and distribution of redundant patterns and their level of un-balancement. (As an example, if a quality score=30 is 90% of all quality scores in the range of 1 to 40, the distribution of quality scores is very unbalanced, but if all 40 possible quality scores have a 2.5% share in the dataset, the distribution is completely balanced). A frequency-based compressor cannot perform optimally unless it is customized and tuned for each FastQ or FastA dataset based on its own distribution, as is the case at the optimizer 210.

The bases 204 are analyzed by the system of the present technology as follows. Using the header 218, meta information about the characteristics of the sequence part of the dataset such as the value of obtained optimal hyperparameters, distribution features and the number of various types of irregular symbols in the dataset is stored. Regular bases 214 that comprise the DNA bases 204 mainly consist of adenine (A), cytosine (C), guanine (G), and thymine (T), while RNAs include adenine (A), cytosine (C), guanine (G), and uracil (U). To encode each base in binary format, just 2 bits are preferably required.

Identifiers 208 are transmitted to an identifier compression module 214, where the identifiers 208 are encoded and compressed, exemplarily using the algorithm outlined below. The encoded and compressed identifiers are transmitted from the identifier compression module 214 to the general compressor 234, which is responsible for generating the compressed file, preferably using a lossless, general-purpose compressor (e.g., gzip).

Input: identifiers
Output: compressed identifier (Ident_change_Index, Ident_change_value)
1. Store the identifier of the first read
2. calculate Ident_change_Index for each of tile, xpos and ypos, which demonstrates if they have changed from the previous read. (y: 1, n: 0)
3. calculate Ident_change_value which demonstrates the amount of change (for those have changed) for tile, xpos and ypos, separately.

The quality scores 206 and the sequence bases 204 are transmitted to a first read splitter 210 and a second read splitter 212, respectively. The first and second read splitters 210, 212 split long reads of data into smaller reads (segments). Since the segments need to be the same length, depending on the read_length (RL) and desired number of segments, there may be a need to separate a fixed number of nucleotides or quality scores (named extra_len) from the end of the reads first to make the segments the same length. The separated extra part is called an extra segment.

An exemplary embodiment of the read splitter function is described below:
Input: base or quality score sequences
Output: (segmented) base or quality score sequences
1. Calculate num_seg, seg_len, extra_len.

$$\text{num\_seg} = \left\lfloor \frac{RL}{\text{ideal\_len}} \right\rfloor$$

$$\text{seg\_len} = \left\lfloor \frac{RL}{\text{num\_seg}} \right\rfloor$$

$$\text{extra}_{len} = RL - \text{num\_seg} * \text{seg\_len}$$

note: The ideal_len is a hyperparameter that is used to find the suitable length of segment.
2. Each read is split to num_seg segment of seg_len.
3. The extra segments are concatenated together and create a long sequence and then is split to segments of length seg_len and appended to the end of created segments.
note: this function doesn't change the identifier.

Figure 3:
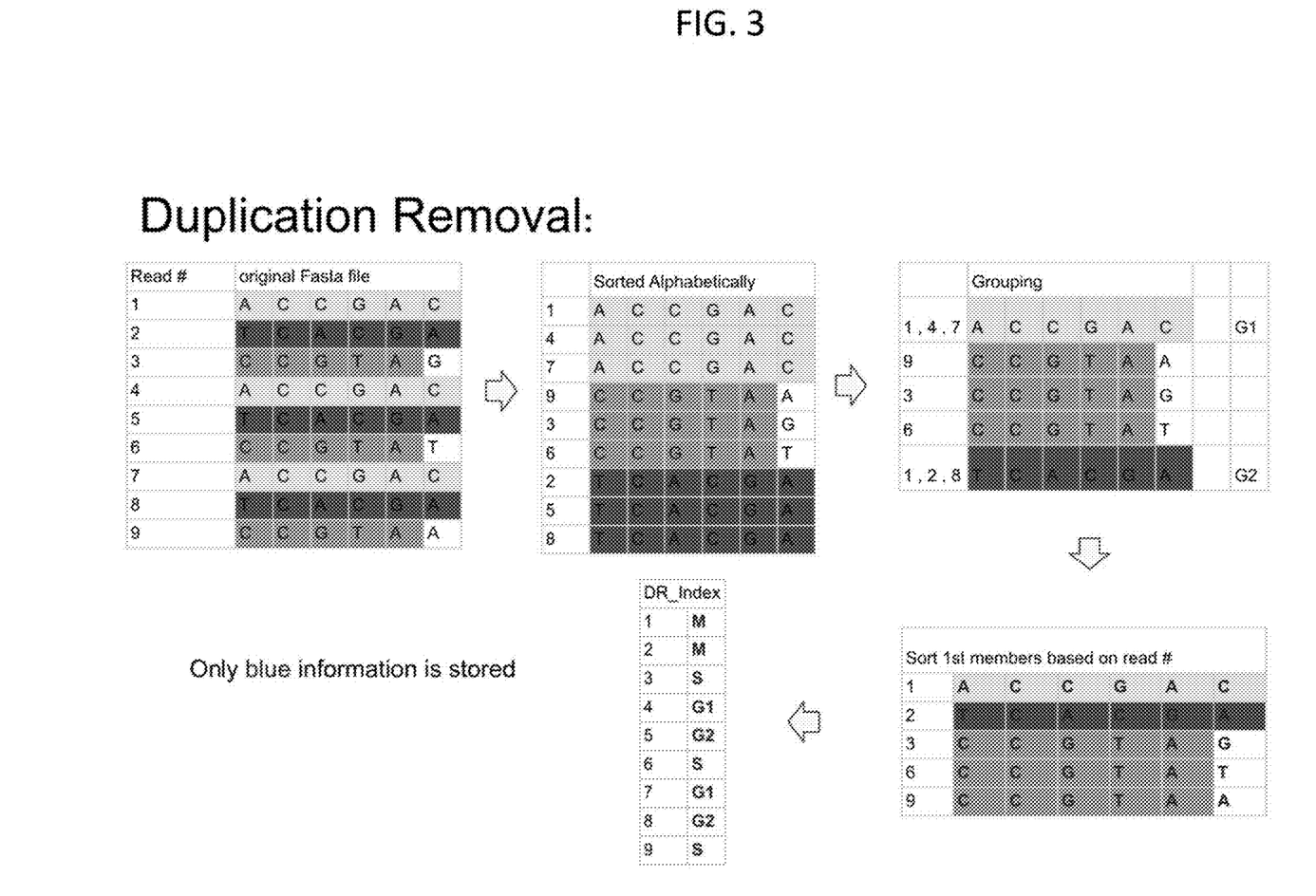
FIG. 3 is a series of tables showing an example of duplication removal performed by the system of the present invention.

After the first read splitter 210 and the second read splitter 212 split long reads of the quality scores 206 and the sequence bases 204, the split data from the quality scores 206 is transmitted to a first duplication removal module 216, while the split data from the sequence bases 204 is transmitted to a second duplication removal module 218. An exemplary process for duplication removal is shown in FIG. 3. The first and second duplication removal modules 216, 218 remove duplicate data entries, as shown in the exemplary algorithm below:

Input: base sequences
Output: base_sequences (DR_remaining_reads), DR Auxiliary Info (DR_index)
1. Sort all the input reads alphabetically, but still preserve their read number.
2. Group the reads that are identical (some will be single member and some multi member groups).
3. For each read in the input file, encode the corresponding index from the following table, and then call it DR index file.

| | |
|---|---|
| S | Member of Single groups |
| M | First member of multi groups |
| Gi | Non-first member of $i^{th}$ multi groups |

4. Only the reads with S and M index will be kept (in the original order), called DR_remaining_reads, and others are removed.

Note: multi groups are listed in alphabetical order.

Once the duplicate data entries related to the quality scores 206 are removed by the first duplication removal module 216, the data related to the quality scores 206 is transmitted to the general compressor 234, which is responsible for generating the compressed file, using a lossless, general-purpose compressor (e.g., gzip).

Similarly, once the duplicate data entries related to the sequence bases 204 are removed at the second duplication removal module 218, the data related to the sequence bases 204 may be transmitted directly to the general compressor 234, which is responsible for generating the compressed file, using a lossless, general-purpose compressor (e.g., gzip).

Figure 4:
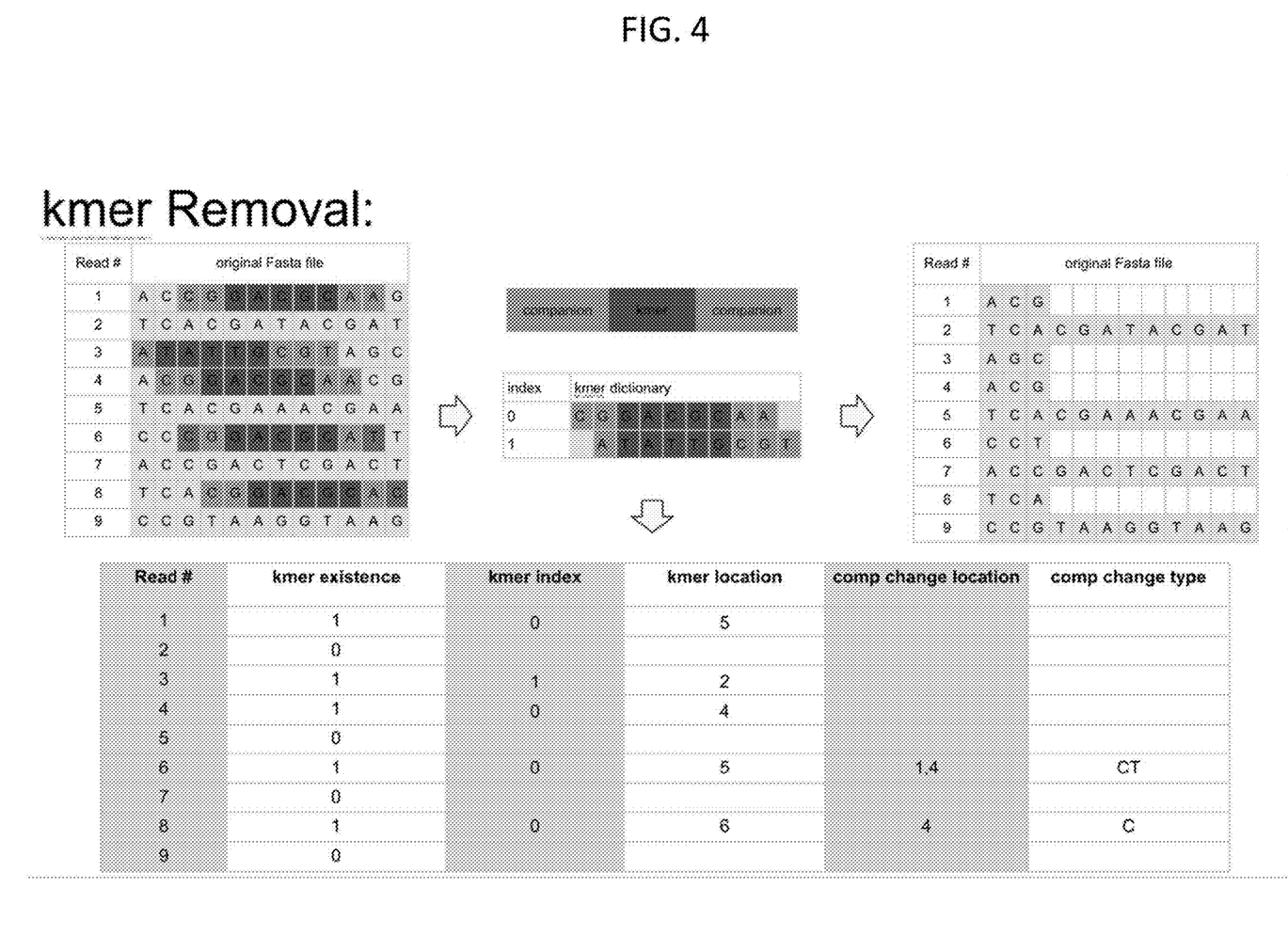
FIG. 4 is a series of tables showing an example of k-mer removal performed by the system of the present invention.

In certain embodiments, the data related to the sequence bases 204 is transmitted from the second duplication removal module 218 to the semi-duplication removal module 220, which removes similar data reads from the data associated with the sequence bases 204. An example process for semi-duplication removal is shown in FIG. 4. An exemplary algorithm used by the semi-duplication removal module 220 is outlined below:

Input: base sequences, default hyperparameter (SDR_diff)
Output: base_sequences (SDR_remaining_reads), SDR Auxiliary Info (SDR_read_numbers, SDR_change_loc), SDR Extra Base Sequences (SDR_change_seq)
1. Sort all the input reads alphabetically, but still preserve their read number.
2. Group the reads that are semi-identical. Here, semi-identical means the first difference between each member of the group with the previous one is not at the location bigger than "SDR_diff". So, some groups will be single and some multi members. In the SDR block, the change is considered the sub sequence starting from the first difference untill the end of the sequence.
Example: seq1: AAAAAAAAAA, seq2: AAAAAAACAA=>changed sub-seq=CAA
3. Create an empty "SDR_change_seq" string and "SDR_change_loc list". The changes from each member of the multi groups with the previous member is appended to the "SDR_change_seq" string and the length of the changed sub-seq is appended to "SDR_change_loc".
4. List the first member of the first groups and multi-groups and sort them based on their read number, call it SDR_remaining_reads.

5. Remove the read number of the first member of the groups from read numbers and then save it as "SDR_read_numbers".

Once similar data reads are removed at the semi-duplication removal module 220, the data may be directly transmitted to the general compressor 234 for lossless compression, transmitted to a random sequence generator module 222 in order to generate a random subset of the data, or transmitted to a dictionary sub-sequence removal module 226. Depending on user settings, the random sequence generator module 222 may take smaller or larger random samples of the data, in order to preserve computing resources while still maintaining the integrity of the system. An exemplary algorithm used by the random sequence generator module 222 is outlined below:

Input: sequence bases, default hyperparameter (random_subset_percentage)
Output: random_subset
1. randomly select random_subset_percent % base sequences
note: random_subset_percent=100 will give the perfect dictionary but smaller samples can give a fairly good dictionary in a shorter amount of time.

Once the random sequence generator module 222 has generated a random sample of the data, it is passed through a sub-sequence dictionary optimizer module 224 that creates the k-mers dictionary.

The high-density k-mers associated with the bases 204 are listed and labeled in binary format in the k-mers dictionary. For each k-mer in the k-mer dictionary, there is an index that labels the k-mer. Those indices are then encoded in binary. During data compression process, it is the index of k-mers that is being recorded, instead of the actual k-mer sequences. The optimal values for a number of k-mers in the dictionary are specified by solving an optimization problem. In an exemplary solution to an optimization problem, an objective function is developed based on the compression algorithm to roughly approximate the compressed size of the random subset of dataset without actual compression. Next, the optimization variables, which are hyperparameters of the compression algorithm, are specified. Using a deterministic or stochastic optimization algorithm, the values of the optimization variables are obtained in a way that the objective function is minimized. Finally, the obtained optimal values are used as the hyperparameter values for compression of the whole dataset.

Dimensionality reduction may also be performed using binary labels from the k-mers dictionary and the regular bases 214 associated with the bases 204. Machine learning algorithms that apply techniques other than dimensionality reduction may be utilized as well, including but not limited to nearest neighbor analysis, Bayesian modeling, regression modeling, support vector machines, and neural networks.

Figure 5:
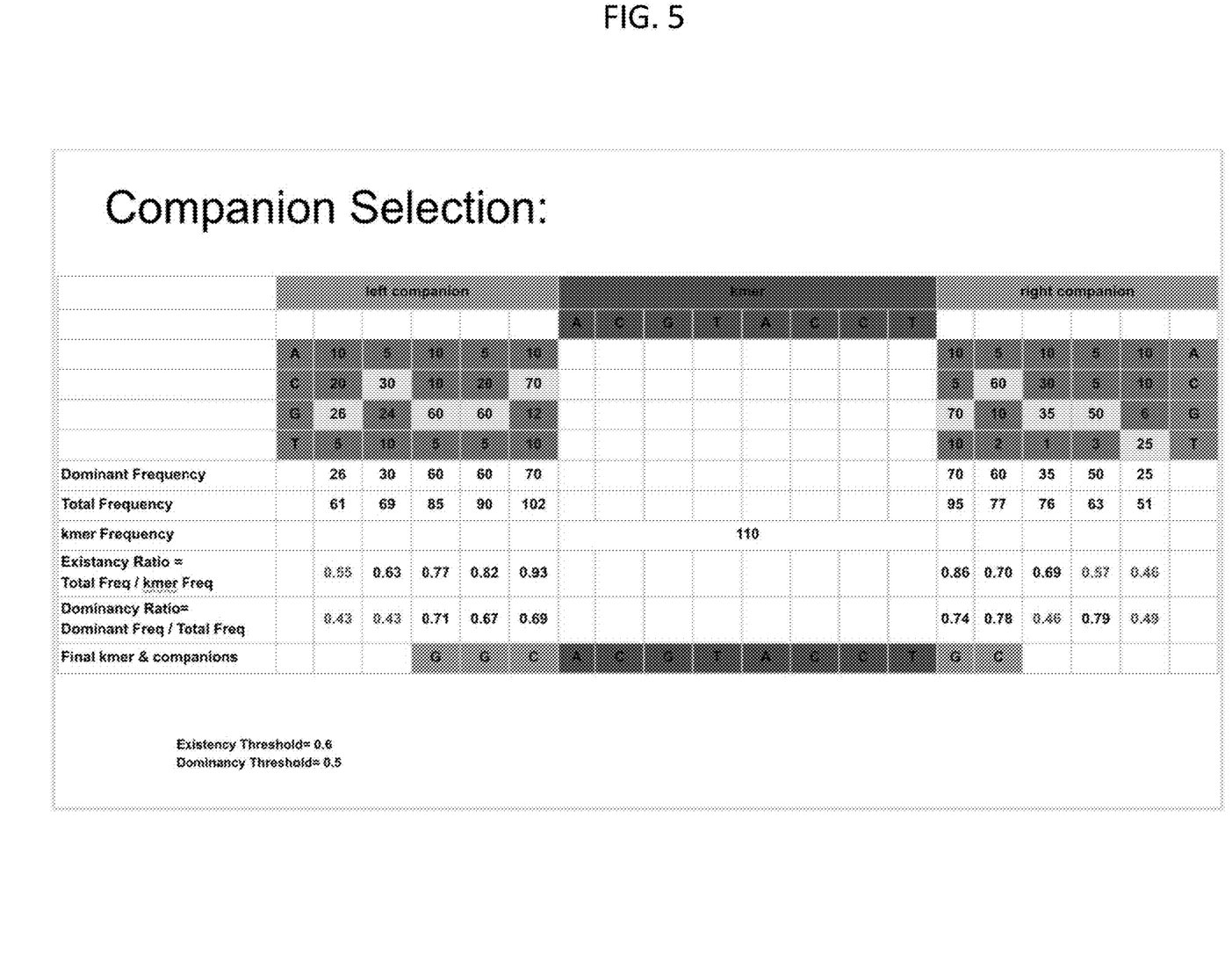
FIG. 5 is a table showing an example of companion selection performed as a part of the companion of k-mers method.

In certain embodiments, the system performs an operation referred to as the "companion of k-mers," in which it predicts what is coming after and before k-mers (left and right companion) and stores them with the k-mers in the dictionary, as shown in FIG. 5. With reference to FIG. 5, during creation of dictionary for k-mers, the system of the present invention searches for the subsequences that have high frequency with exact match in the file. However, for the companions, the system of the present invention searches for high frequency, sufficiently similar subsequences (imperfect match) prior to or after the k-mers. The k-mer and companions can be then selected based on the statistical features presented in the example algorithm. During dictionary creation, the k-mers are counted in the case of a "perfect match," along with counting the companion in case they are "dominant" and "statistically significant" in that position relative to k-mer.

Figure 6:
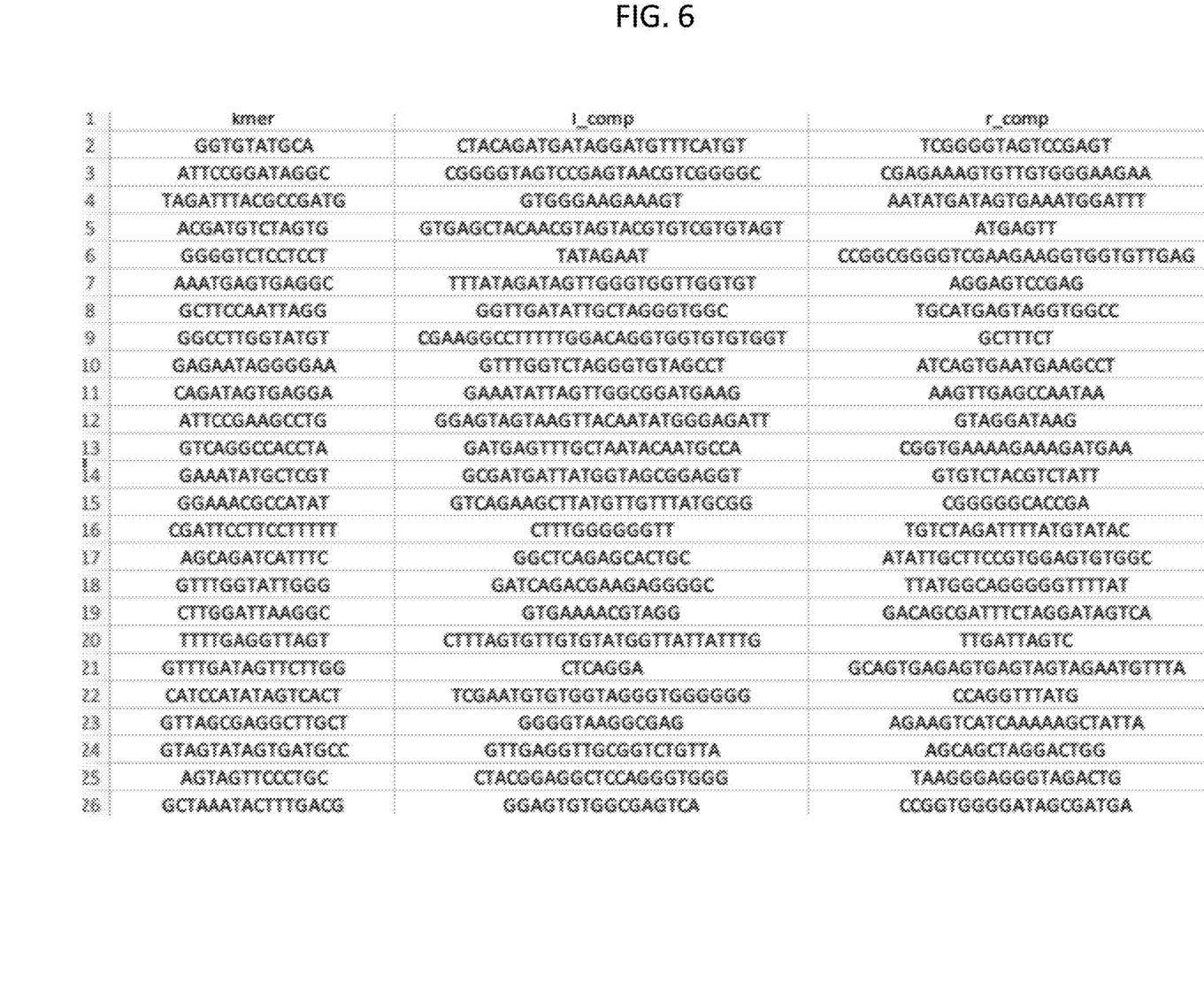
FIG. 6 is a table showing an example of a final k-mer dictionary.

In addition, in certain embodiments, the system performs a dynamic dictionary creation process. For each sub-sequence (mer) that is added to the dictionary, there are internal competitions between k-mers for each k value in the k-list (e.g., if we have k-list=[10, 15, 20], there will be three internal competitions, one for each k-value). That internal competition is followed by an external competition between the winner of internal competitions (in this example, best 10-mer, best 15-mer and best 20-mer). The winner of the external competitor will be added to the final dictionary, an example of which is shown in FIG. 6. The length of the final dictionary is specified during the dictionary creation process based on the optimization cost function. An exemplary algorithm for dynamic dictionary creation is outlined below:

Input: random subset of sequences, default hyperparameters: (k-list, existancy_threshhold, dominancy_threshhold).
Output: k-mer dictionary
Counting:
1. create an array of length len(kiit) called preliminary_dict, for each k value in the $k_{list}$ the array element will be a k-mer dictionary as follow:
[key: k-mer sequence, value: k-mer frequency]
Initialization:
2. For each k value in the k-list
a. Count the frequency of k-mers
b. Sort the k-mers based on their frequency
c. Count the frequency of each nucleotide (A, C, G and T) at positions 1:(RL−k) next and before top sorted k-mers
d. For each x top k-mers, consider the first (y_right and y_left) nucleotides in the right and left side of the k-mer as prel companion_right and prel_companion_left that can pass following two thresholds.
existency_ratio (k-mer(i),position(j, RL (right or left)))= (number of reads that have k-mer(i) and any nucleotide in position (j) in RL side of k-mer)/(number of reads that have k-mer(i))
dominancy_ratio (k-mer(i),position(j, RL (right or left)))=(number of reads that have k-mer(i) and the dominant nucleotide in position (j) in RL side of k-mer)/(number of reads that have k-mer(i) and any nucleotide in position (j) in RL side of k-mer(i))
3. calculate the (average+2*standard_deviation) of (y_right(k-mer(i)+y_left(k-mer(i))) is considered as the initialized length of companion for all k-mers for each k-value.
Competition:
In the preliminary dictionary, the k-mers are sorted based on the frequency of k-mers. However, they are actually sorted based on the k-mer+initialized companions also, because the length of the initialized companion for all k-mers is the same.
4. create an empty list called read_list. It will be filled with the read number of the reads that contain the final dictionary k-mers.
Internal Competition:
5. for each k-value in the k-list:
a) obtain the internal compression_score for all k-mers.
internal_compression_score=frequency(k-mer)*[1+len (companion)/k]
b) obtain the updated frequency of the k-mers. Updated frequency=initial frequency−frequency of k-mer in the reads included in the red_list.

c) obtain the actual companion (right and left) based on existancy_threshold and dominancy_threshhold.

d) update the internal_compression_score just for the top k-mer, if it was bigger than the current internal_compression_score of the second rank, the top one is selected as the winner of internal competition for this k-value. If the score of the top k-mer was less than the second's, we re-sort them based on score, i.e., the top one goes to the rank that it belongs to, based on its updated score, and then all the k-mers beyond that score shift one rank up. This step continues until the internal winner is selected.

External Competition

6. The winners of the internal competition of each k-value should compete with each other based on the external_compression_score. The k-mer that has higher value goes to the final dictionary.

7. calculate the cost_function.

Note: Following formula give the $Size_{compressed\_seqs}$ as a function of dict_len for the existing distribution of k-mers in the FASTQ/A file.

$$Size_{compressed\_seqs} = Size_{original\_Seqs} + Size_{kmer\_all} + Size_{companion\_all}$$

$$Size_{original\_seqs} = 2 * nR * RL$$

$$Size_{kmer\_all} = -Size_{kmer\_seqs} + Size_{kmer\_location} + Size_{kmer\_index} + Size_{kmer\_existence} + Size_{kmer\_dictionary}$$

$$Size_{Companion\_all} = -Size_{Companion\_Seqs} + Size_{Companion\_location\_change} + Size_{Companion\_number\_chanage} + Size_{Companion\_type\_chanage} + Size_{companion\_dictionary}$$

$$Size_{kmer\_seqs} = \sum_{i=0}^{dict\_len-1} Frequency_{kmer(i)} * (2 * k_{kmer(i)})$$

$$Size_{kmer\_location} = \sum_{i=0}^{dict\_len-1} Frequency_{kmer(i)} * \lceil(RL - k_{kmer(i)})\rceil$$

$$Size_{kmer\_index} = \sum_{i=0}^{dict_{len}-1} \left[Frequency_{kmer(i)} * len(Huf\_Ind_{kmer(i)})\right]$$

$$Size_{Existence} = nR$$

$$Size_{kmer\_dictionary} = \sum_{i=0}^{dict_{len}-1} \left[(2 * k_{kmer(i)}) + \lceil\log_2^{(len(k_{list}))}\rceil + len(Huf\_Ind_{kmer(i)})\right]$$

$$Size_{compressed\_seqs} = \sum_{i=0}^{dict_{len}-1} Frequency_{kmer(i)} * \left(2 * len(companion_{kmer(i)}^{1st})\right) -$$

$$\eta^{penalty} * \left[\sum_{p=1}^{len(companion_{kmer(i)}^{1st,R})} nondominancy\_ratio(p) + \sum_{q=1}^{len(companion_{kmer(i)}^{1st,L})} nondominancy\_ratio(q)\right]$$

$$Size_{companion_{dictionary}} = \sum_{i=0}^{dict_{len}-1} \left(2 * 2 * len(companion_{kmer(i)}^{1st})\right) + \left[\log_2^{RL-k_{kmer(i)}}\right] + \left[\log_2^{RL-k_{kmer(i)}-len(companion_{kmer(i)}^{1st,R})}\right]$$

Existence: a vector of length nR, to show which reads include any of final_seq_dictionary k-mers (value=1) and those that don't (value=0).

$Dict\_Index_{kmer}$: binary index of k-mers in the dictionary for each read having Existence=1.

$Location_{kmer}$: The location of the starting point of the k-mer in the sequence read, in binary.

note: the size of location for the larger k-mers can be smaller, because for example if k=20 and RL=50, the starting point of the k-mer cannot be larger than 31 and so can be encoded with 5 bits, but if k=18, the starting point can be up to 33 which needs 6 bit to encode in binary dict_len: number of k-mers in the final seq dictionary $\eta^{penalty}$: the penalty factor for the fraction of nucleotides that doesn't match the companion. This penalty factor is because during encoding when companion(s) don't match the dominant companion (companion_1st in the dictionary) not only do we need to save the type of correct nucleotides, but also, we need to store the location and number of changes. This penalty factor helps to include the cost of companion mismatch in calculation of cost function).

note: The dictionary optimizer obtains the optimum dict_len value to have the $Size_{compressed\_seqs}$ minimized.

8. If any of the stopping criteria is met, freeze the final dictionary at the optimal point, and exit this function. If not, go ahead.

Stopping Criteria:

a) Increase in cost function for specific number of iterations (in this case the optimal dictionary length will be the current iteration number minus patient_actor).

b) Reach to max_dict_len iterations (in this case the optimal dictionary length will be the current iteration number).

9. The read list gets updated.

The loser of the external competition will be returned to the internal competition as the top ranked (stage 4) and its score will be updated.

Figure 7:
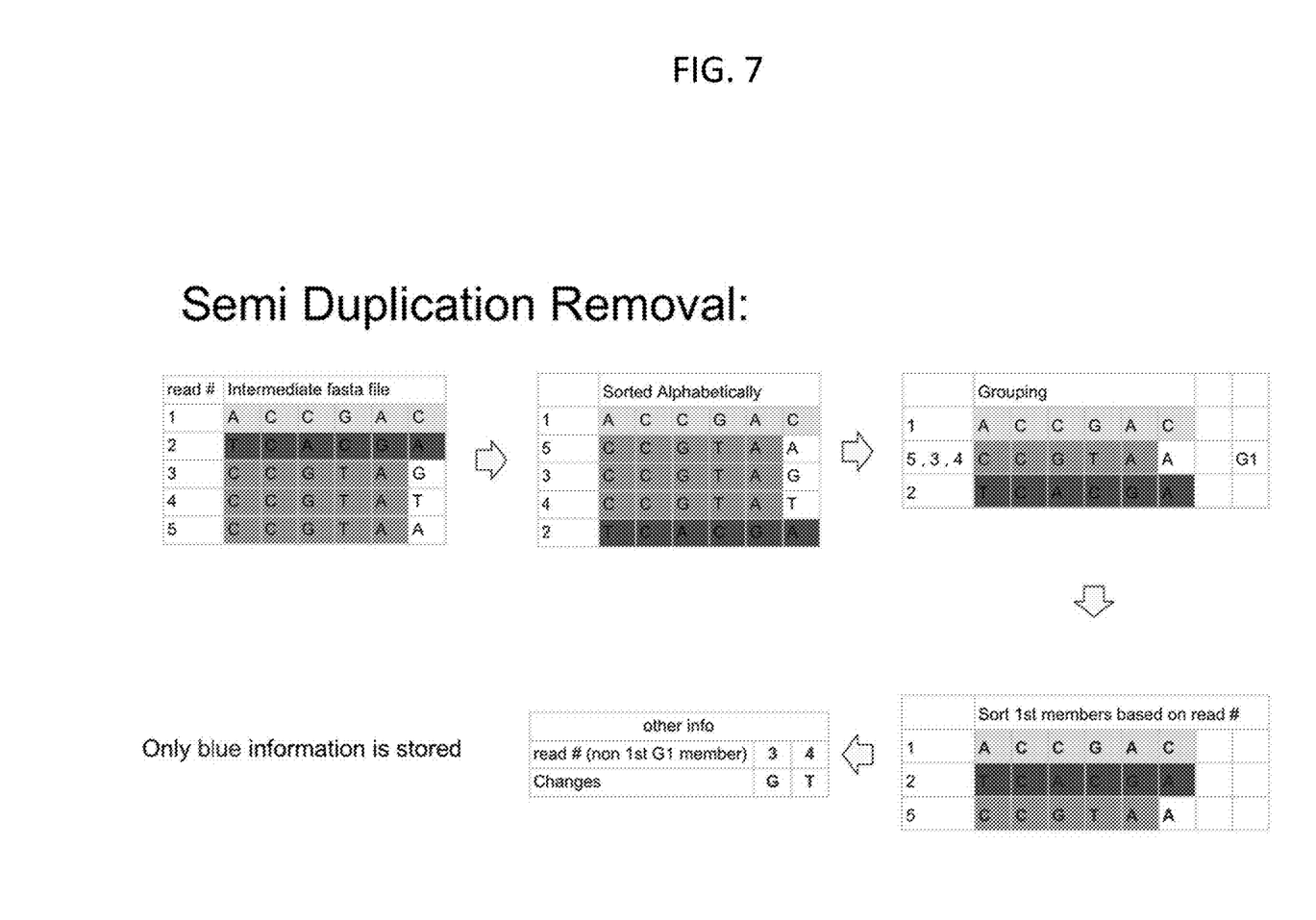
FIG. 7 is a series of tables showing an example of how semi-duplication removal is performed on similar data reads by the system of the present invention.

The data generated from the sub-sequence dictionary optimizer module 224 is passed to the dictionary sub-sequence removal module 226. The dictionary sub-sequence removal module 226 is responsible for removing certain k-mers from the dictionary, as shown in FIG. 7. An exemplary algorithm used by the dictionary sub-sequence removal module 226 is described below:

Input: base sequences, k-mer dictionary.

Output: base_sequences (untouched seqs), Dr Auxiliary Info (k-mer dict_exist, k-mer_dict_index, k-mer_dict_loc, comp_loc_change, comp_num_change) k-mer Removal Extra Sequences (k-mer_dict_remain seqs, comp_type_change)k-merk-merk-merk-mer 1. create seven empty strings to encode the information regarding the sequences that include dictionary k-mers:

k-mer_dict_exist (encodes existence of dictionary k-mers in the read)

k-mer_dict_index (encodes index of dictionary k-mers in the read)

k-mer_dict_loc (encodes starting location of dictionary k-mers in the read)

comp_num_change (encodes number of mismatches with a companion of the dictionary k-mers in the read)

comp_loc_change (encodes location of mismatch with a companion of the dictionary k-mers in the read)

comp_type_change (encodes correct nucleotide type for the mismatch with a companion of the dictionary k-mers in the read)

k-mer_dict_remain_seq (encodes remaining part of the reads after removing the k-mers and companions)

unloched_seqs (sequences which didn't include any k-mer from dictionary)
2. encode 1 bit per read as k-mer_dict_exist, 0: if the read doesn't include any k-mer from final k-mer dictionary; 1: if it does include.
3. If a final dictionary k-mer does exist in the read:
  a. encode the dictionary index of the k-mer in k-mer dict_index.
  b. encode the location of k-mer's first base in the read, in k-mer dict_loc.
  c. find the number of mismatches between the final dictionary predicted companion vs the actual companion of the k-mer in the read, and encode that in comp_num_change.
  d. encode the location of differences detected in the previous step in comp_loc_change.
  e. encode the nucleotide type of differences detected in step 3.c in comp_loc_type.
  f. encodes the remaining part of the reads after removing the k-mers and companions in k-mer_dict_remain_seq.
     note: in this version of the compression technique, up to one k-mer is considered in each read, and if more than one exists in one read, the one that has higher ranking in the k-mer_dictionary is selected because it will conclude in a higher compression.

From the dictionary sub-sequence removal module 226, the modified data is transmitted to a second semi-duplication removal module 228, which removes similar data reads from the data associated with the sequence bases 204, as described above. In certain embodiments, the system uses the second semi-duplication module 228, which is the same process as the first semi-duplication removal module with different parameter values and in a reverse sequence order 220.

Once similar data reads are removed from the data, the data is transmitted to a sequence regularizer module 230, which is responsible for encoding irregular nucleotides. Irregular nucleotides are those that are not A (adenosine), C (cytosine), G (guanine), or T (tyrosine). An exemplary algorithm used by the sequence regularizer module 230 is described below:

Input: base sequences and/or extra sequences.
Output: base sequences and/or extra sequences, sequence Regularizer Auxilialy ifo(irregular_reads_existence, irregular_nit_number, irregular_nt_location and non_N irregular_nt_info).
note: by irregular nucleotide we mean any nucleotide other than A, C, G and T.
1. create empty strings, called irregular_reads_existance, irregular_nt_number irregular_nt_location and non_N_irregular_nt_info to encode existence, number, location of the irregular nucleotides and the information of non-N irregular nucleotides.
2. irregular_reads_existence encode one bit for each read, 0: no irregular nucleotide in this read, 1: there is at least one irregular nucleotide.
3. irregular_nt_number encode number of irregular nucleotides for each irregular reads.
4. irregular_nt_location, encode position of each irregular nucleotide in the read
5. non_N_irregular_nt_info, by default all irregular nucleotides letters are assumed to be N (which is the most common irregular nucleotide), and just if any irregular non-N nucleotide was observed its information in encoded as non_N_irregular_nt_info (irregular_read_index ($i^{th}$ irregular read), irregular_nt_location index ($i^{th}$ irregular nucleotide in that irregular read), type).
6. non_N_irregular_nt_info=[irregular_read_index, irregular_nt_location index, type]

Once the irregular nucleotides are encoded at the sequence regularizer module 230, the data is transmitted to the sequence binary encoding module 232, which is responsible for encoding the base sequences 204 in binary. An exemplary algorithm used by the sequence binary encoding module 232 is described below:

Input: base sequences.
Output: binary_base sequences
1. The base sequences are encoded in binary using following hash table:

TABLE 2 nucleotides binary encoding hash table

| nucleotide | Binary code |
| --- | --- |
| A | 00 |
| C | 01 |
| G | 10 |
| T | 11 |
| Irregular nucleotides | 00 | note: irregular nucleotides are temporarily stored as A: [0 0] since their info is recorded separately.

Encoded data from the sequence binary encoding module 232 is transmitted to the general compressor 234. At the general compressor 234, the encoded binary dataset is compressed again with a lossless, general-purpose compressor (e.g., gzip). The result is a compressed FastQ/A file 236. In various embodiments, data may also be transmitted directly to the general compressor 234 from one or more of the first semi-duplication removal module 220, the subsequence dictionary optimizer 224, the dictionary sub-sequence removal module 226, the second semi-duplication removal module 228, and/or the sequence regularizer module 230. An exemplary algorithm for the general compressor is described below:

Input: Sequence Regularizer Auxiliary Info, k-mer Removal Auxiliary Info, k-mer Dictionary Auxiliary Info, SDR Auxiliary Info, DR Auxiliary Info, Quality Score sequences, Binary Base sequences, compressed identifiers
Output: final_compressed file The target is to have maximum compression after the general compressor and not before that. Therefore, although further compression in domain-specific compression is possible, they are not included in the process because of their insignificant or negative effect on the final file.

Hyperparameters Used in Optimization:

k-list
random_subset_percentage
existency_threshhold
dominancy_threshhold
patient_factor
max_dict_len
$\eta^{penalty}$
ideal_len
N* (1st SDR block)
N* (2nd SDR block)

The disclosed processes have a number of benefits over the prior art. Those benefits include:

(1) Customized Compression: The encoding protocol is not rigid. Instead, the encoding protocol (and the corresponding decoding protocol) is optimally tuned based on the characteristics of each specific dataset.
(2) Compression rate: The disclosed encoding protocol yields a higher compression rate than general compressors and genomic data compressors.
(3) Reference-free: The compressor is reference-free, eliminating the need to perform the computationally expensive process of aligning the sequence to the reference genome.
(4) Zero-loss: The entire encoding/decoding process is lossless.
(5) FastA files: The encoding algorithm is able to compress the sequence data independently. Accordingly, in addition to FastQ files, the compressor can also be used to compress FastA files.
(6) Non-N irregular bases: irregular bases are not limited to N in the encoding process of this method.
(7) Compression time: The disclosed encoding protocol yields a faster compression than general compressors and genomic data compressors.

The foregoing description and drawings should be considered as illustrative only of the principles of the invention. The invention is not intended to be limited by the preferred embodiment and may be implemented in a variety of ways that will be clear to one of ordinary skill in the art. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention. All references cited herein are incorporated by reference.

The invention claimed is:

1. A method for data compression of genomic data comprising:
    receiving a data file comprised of sequence bases, quality scores, and identifiers, the sequence bases comprising regular bases and irregular bases, the regular bases comprising adenine (A), cytosine (C), guanine (G), and thymine (T);
    applying an optimization algorithm to the quality scores, sequence k-mers from the sequence bases, and the identifiers;
    splitting long reads of the sequence bases and the quality scores into smaller segments;
    deleting duplicated and semi-duplicated reads for the sequence bases and the quality scores;
    performing a dimensionality reduction on the sequence bases;
    storing a template of the identifier that is consistent across the data file;
    detecting and storing the location and type of each irregular base;
    encoding the data file in a binary format such that each regular base is represented by one of the four two-digit binary numbers and all irregular bases are represented by one of the four two-digit binary numbers; and
    compressing the encoded data file.

2. The method of claim 1, wherein the identifiers are comprised of sequencing run data and cluster data.

3. The method of claim 1, wherein the quality scores comprise the sequence of quality values for the sequence bases.

4. The method of claim 1, wherein:
    the irregular bases include N and a plurality of additional irregular bases; and
    storing the location and type of each irregular base comprises storing the location of each irregular base and the type of each additional irregular base.

5. The method of claim 4, wherein dimensionality reduction is performed using binary labels from a k-mers dictionary and the base sequences.

6. The method of claim 1, wherein the data file is a FastQ file or a FastA file.

7. The method of claim 1, wherein the optimization algorithm determines an optimal value for encoding algorithm hyper-parameters, the sequence k-mers from the bases, and the identifiers.

8. The method of claim 1, wherein the optimization algorithm is a function of protocol hyperparameters and distribution indices of the data file.

9. The method of claim 1, wherein the compression is reference-free.

10. The method of claim 1, wherein the compression is tuned based on characteristics of the data file.

11. A non-transitory computer storage medium that stores a program thereon that causes a computer to execute a process comprising:
    receiving a data file comprised of sequence bases, quality scores, and identifiers, the sequence bases comprising regular bases and irregular bases, the regular bases comprising adenine (A), cytosine (C), guanine (G), and thymine (T);
    applying an optimization algorithm to the quality scores, sequence k-mers from the sequence bases, and the identifiers;
    splitting long reads of the sequence bases and the quality scores into smaller segments;
    deleting duplicated and semi-duplicated reads for the sequence bases and the quality scores;
    performing a dimensionality reduction on the sequence bases;
    storing a template of the identifier that is consistent across the data file;
    detecting and storing the location and type of each irregular base;
    encoding the data file in a binary format such that each regular base is represented by one of the four two-digit binary numbers and all irregular bases are represented by one of the four two-digit binary numbers; and
    compressing the data file, wherein the compression is lossless.

12. The non-transitory computer medium of claim 11, wherein the identifiers are comprised of sequencing run data and cluster data.

13. The non-transitory computer medium of claim 11, wherein the quality scores comprise the sequence of quality values for the sequence bases.

14. The non-transitory computer medium of claim 11, wherein:
    the irregular bases include N and a plurality of non-N irregular bases; and
    storing the location and type of each irregular base comprises storing the location of each irregular base and the type of each non-N irregular base.

15. The non-transitory computer medium of claim 14, wherein dimensionality reduction is performed using binary labels from a k-mers dictionary and the regular bases.

16. The non-transitory computer medium of claim 11, wherein the data file is a FastQ file or a FastA file.

17. The non-transitory computer medium of claim 11, wherein the optimization algorithm determines the optimal hyperparameters values for each of the quality scores, the sequence k-mers from the bases, and the identifiers.

18. The non-transitory computer medium of claim 11, wherein the optimization algorithm is a function of protocol hyperparameters and distribution indices of the data file.

19. The non-transitory computer medium of claim 11, wherein the compression is reference-free.

20. The non-transitory computer medium of claim 11, wherein the compression is tuned based on characteristics of the data file.

* * * * *